United States Patent [19]

Moon et al.

[11] Patent Number: 4,845,040
[45] Date of Patent: Jul. 4, 1989

[54] METHOD AND APPARATUS FOR ANALYZING DIFFERENT SULPHUR FORMS

[75] Inventors: Kwang S. Moon, Kanata; Louis L. Sirois, Ottawa, both of Canada

[73] Assignee: Canadian Patents and Development Limited/Societe Canadienne Des Brevets Et D'Exploitation Limitee, Ottawa, Canada

[21] Appl. No.: 119,915

[22] Filed: Nov. 13, 1987

Related U.S. Application Data

[63] and a continuation-in-part of Ser. No. 809,737, Dec. 17, 1985.

[30] Foreign Application Priority Data

Dec. 17, 1984 [CA] Canada ................................. 470308

[51] Int. Cl.$^4$ ..................... G01N 33/00; G01N 31/12
[52] U.S. Cl. ..................... 436/120; 422/78; 422/80
[58] Field of Search ..................... 436/119–123, 436/155–160; 422/78, 119, 80

[56] References Cited

U.S. PATENT DOCUMENTS

| | | | |
|---|---|---|---|
| 3,393,051 | 7/1968 | Kerver | 436/119 |
| 3,847,546 | 11/1974 | Paul | 23/230 PC |
| 3,904,364 | 9/1975 | Dodson | 23/230 R |
| 3,985,505 | 10/1976 | Bredeweg | 23/230 PC |
| 4,213,763 | 7/1980 | Madec et al. | 23/230 EP |
| 4,221,569 | 9/1980 | Kebbekus | 436/120 |
| 4,277,368 | 7/1981 | Amy et al. | 436/122 |

Primary Examiner—Barry S. Richman
Assistant Examiner—T. J. Wallen
Attorney, Agent, or Firm—Finnegan, Henderson, Farabow, Garrett & Dunner

[57] ABSTRACT

A method and apparatus are described for quantitatively determining the different forms of sulphur present in a solid matrix, e.g. coal. The novel method comprises intimately mixing finely divided coal with a finely divided solid diluent material, e.g. silica, which is inert to sulphur under reaction conditions. This mixed sample is then burned within a confined combustion zone at a predetermined elevated temperature and the combustion gases from the combustion chamber are continuously removed. These gases are passed through an infrared analyzer which continuously monitors the intensity of the infrared spectra for sulphur oxycompounds in the combustion gases. The infrared intensity is measured as a function of evolution time of sulphur oxycompound from the sample to obtain peaks in an infrared intensity-time pattern indicative of different forms of sulphur.

9 Claims, 6 Drawing Sheets

METHOD AND APPARATUS FOR ANALYZING DIFFERENT SULPHUR FORMS

BACKGROUND OF THE INVENTION

This invention relates to a method and apparatus for quantitatively determining the different forms of sulphur present in a matrix, such as coal, and is a continuation-in-part of U.S. application Ser. No. 809,737, filed Dec. 17, 1985.

One of the more serious environmental problems throughout the world is air pollution due to the emission of sulphur oxides when sulphur-containing fuels are burned. It is now widely recognized that sulphur oxides are particularly harmful pollutants, producing what is now known as acid rain.

Coal remains one of the world's most important fuel sources and large quantities are burned in thermogenerating plants for conversion into electrical energy. Many coals contain substantial amounts of sulphur which generate unacceptable amounts of sulphur oxides on burning. Coal combustion is by far the largest single source of sulphur dioxide pollution in the United States.

The sulphur content of coal, nearly all of which is emitted as sulphur dioxides during combustion, is present in essentially three forms: pyritic sulphur, organic sulphur and sulphate sulphur. Distribution between the different forms of sulphur varies widely among various coals and can even vary quite substantially within a single coal deposit.

It is, of course, highly desirable to be able to remove substantial portions of the sulphur present in coal before the coal is burned. Since the different forms of sulphur must be removed by different techniques, how a given supply of coal will be processed will be largely dependent on the relative proportions of the different forms of sulphur present in the coal. The present ASTM methods of analyzing for the different forms of sulphur present in coal are exceedingly time consuming and require highly trained personnel. For instance, the current practice utilizes wet analysis of pyritic and sulphatic sulphur to get the content of organic sulphur by difference from the total sulphur contents.

There are many different instruments available on the market that can quickly analyze the total sulphur content of coal. For instance, one commercial analyzer oxidizes the coal sample in a resistance furnace, where the sulphur in the coal is combusted to a gas of sulphur oxycompounds ($SO_x$) which is detected by an infrared detector. These sulphur oxycompounds are primary sulphur dioxide together with minor amounts of other sulphur oxycompounds. However, this analyzer is capable only of giving the total infrared intensity, time integrated as the total sulphur content.

There is a need for a method and apparatus which can quantitatively determine the different forms of sulphur present in a matrix, such as coal, as simply as total sulphurs can now be determined. With that object in mind, the present inventors developed a method for quantitatively determining the different forms of sulphur present in a sulphur containing material, such as coal, in which a finely divided sulphur-containing sample was burned within a confined combustion chamber. This combustion chamber was at a predetermined elevated temperature, and the combustion gases from the combustion chamber were continuously removed. These removed combustion gases were passed through an infrared analyzer which continuously monitored the intensity of the infrared spectra for $SO_x$ in the combustion gases. The infrared intensity was measured as a function of evolution time of $SO_x$ from the coal sample to obtain peaks in an infrared intensity-time pattern indicative of different forms of sulphur. Based upon the shape of these pattern peaks and the area under the peaks, the quantity of each form of sulphur in the sample was determined.

The above study showed that the different forms of sulphur within coal or other matrix have sufficiently different oxidation or dissociation rates that these can be detected and measured on the basis of $SO_x$ emissions during oxidation. The different forms of sulphur can be shown as separate and distinct peaks on an infrared spectro-chronogram. Thus, the area under the total curve of such spectro-chronogram represents the total sulphur content of the sample and when the different peaks in the curve are resolved into individual curves, the areas under the individual curves can be identified with the amounts of the different forms of sulphur in the total sample. The multi-peak curve can be resolved into individual curves by known techniques utilizing microprocessor technology.

However, there was a major difficulty with the above procedure in that replicate spectro-chronograms on a common test sample varied widely in characteristics. This poor reproducibility of spectro-chronographic results made the deconvolution of different sulphur peaks virtually impossible.

SUMMARY OF THE INVENTION

According to the present invention, the above problem was solved by intimately mixing the finely divided solid sulphur containing sample, e.g. coal, with a finely divided solid diluent material inert to sulphur under reaction conditions. This mixed sample was then burned within a confined combustion zone at a predetermined elevated temperature and the combustion gases from the combustion chamber were continuously removed. These removed combustion gases were passed through an infrared analyzer which continuously monitored the intensity of the infrared spectra for $SO_x$ in the combustion gases. The infrared intensity was measured as a function of evolution time of $SO_x$ from the sample to obtain peaks in an infrared intensity-time pattern indicative of different forms of sulphur. With the mixed sample of the present invention, reproducibility of spectro-chronograms improved dramatically.

It is believed that the reason for this improvement in results is that when powdered coal is tested without a solid inert diluent, erratic high local temperatures are created which interfere with the orderly burning of the different sulphur forms within the coal sample. It is believed that the presence of the small particles of inert diluent uniformly mixed among the coal particles protects the coal from the erratic high local temperatures.

The finely divided solid diluent material is preferably used in an excess relative to the coal with a ratio of finely divided solid inert diluent material to coal of at least 2:1 being preferred. Particularly good resolution between different sulphur peaks is obtained at a finely divided solid inert diluent to coal ratio of 5 to 10:1. Increasing the content of inert diluent beyond this level generally results in the broadening of all peaks of the spectro-chronograms, allowing the use of higher temperatures in the reaction chamber. A variety of different materials may be used as the solid inert diluent and silica has been found to be particularly desirable because it provides excellent results while being readily available and inexpensive. Other non-catalytic inert materials may also be used.

For best results, both the coal sample and the inert diluent should be very finely divided, e.g. in the form of powders. Thus, they generally should have particle sizes of less than 60 μm, with particle sizes of less than 10 μm being particularly preferred. The coal and the inert diluent must be thoroughly blended together so that the diluent particles are well distributed throughout the coal particles. This finely divided mixture is then thinly spread in a uniform layer in a sample container, e.g. a sample boat.

The temperature in the combustion chamber can change the peak positions of the spectro-chronograms, as well as the characteristics or shape of the curves. Thus, the peaks become broader and lower at lower chamber temperatures, and with increasing temperatures, the peaks become more sharply defined and the oxidation and/or dissociation kinetics become faster. Preferably the temperature or the combustion chamber is maintained within the range of about 500° C. to 2000° C. Within this general range, an optimum temperature is selected to provide the best definitions of the different components.

The invention also relates to an apparatus for carrying out the above method and comprising (a) a combustion furnace including a combustion chamber for receiving a finely divided sample of sulphur-containing material and for combusting said sample to form combustion gases containing $SO_x$, means for controlling the temperature of the combustion chamber and means for feeding oxygen to the combustion chamber at a controlled rate, (b) conduit means connected to an outlet of said combustion chamber for continuously removing combustion gases from the combustion chamber, (c) detector means for detecting $SO_x$ concentration of gases passing through said conduit and for generating output signals indicative of said concentration at short time intervals during substantially the total period of combustion gas production from said sample, and (d) processor means for receiving the output signals from (i) the $SO_x$ concentration detector and (ii) time of combustion gas production and determining therefrom the quantity of each form of sulphur in the sample.

A series of experiments were conducted on a modified "LECO SC-32 Sulphur Detector". In the conventional operation of this analyzer, the output of the device (inverse of infrared adsorption intensity for a fixed wavelength of $SO_2$) is collected in the form of digital data to arrive at the total sulphur content of a coal sample. For the present studies, the above analyzer was modified so that the infrared signal output was continuously recorded as a function of oxidizing time to give spectro-chronograms.

DESCRIPTION OF THE PREFERRED EMBODIMENTS

In the drawings which illustrate the invention:

Figure 1:
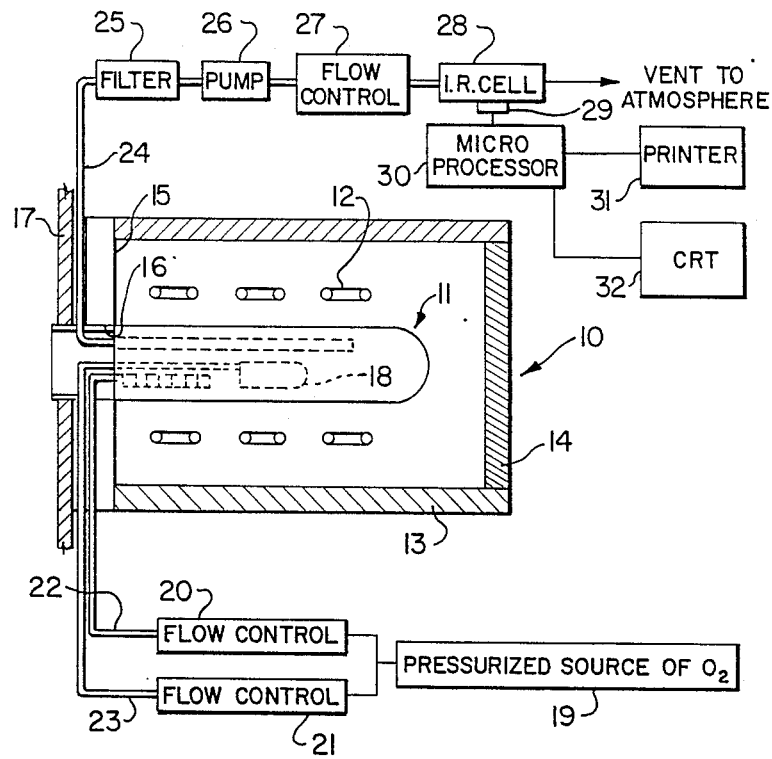
FIG. 1 is a block diagram of components forming the apparatus of the invention.

Referring to FIG. 1, the system includes a combustion furnace 10 with a combustion chamber 11 positioned within the furnace. The furnace 10 is a resistance-type furnace having resistance heating elements 12. The heating elements and combustion chamber are housed within a refractory block including side walls 13, a rear wall 14, and a front wall 15 having an access opening 16 through an instrument front panel 17. The refractory linings of the furnace 10 include a floor and a top. Thus, the combustion chamber 11 is totally enclosed within the refractory lining of the furnace. The system includes a pressurized source 19 of oxygen gas coupled to a pair of flow controllers 20 and 21 which supply the oxygen gas to the combustion chamber 11 via supply conduits 22 and 23 respectively. Thus, the specimen material is combusted by furnace 10 in the presence of oxygen to convert the sulphur contained in the sample to $SO_x$ for subsequent analysis.

Gases from the specimens being combusted within boat 18 in the combustion chamber 11 are withdrawn by a discharge tube 24 which extends into the combustion chamber 11 and communicates with a filter 25, a pump 26 for drawing the gas through the filter and a flow controller 27 for adjusting the flow rate of gas to an IR cell 28. The gas from IR cell 28 is vented to the atmosphere and this IR cell includes a detector 29 which is electrically coupled to a microprocessor 30 for receiving signals from the detector 29.

The microprocessor 30 also is connected to a timer and to the controls of the furnace so that the microprocessor receives signals determining the concentration of $SO_x$ in the gas and signals indicating the time of combustion. The microprocessor is capable of determining from these signals the quantity of each form of sulphur in the sample. It may also be connected to a printer 31 and/or CRT display 32 which can illustrate the results in the form of a spectro-chronogram.

The following examples are provided to more specifically illustrate the invention described herein.

EXAMPLE 1

Figure 2:
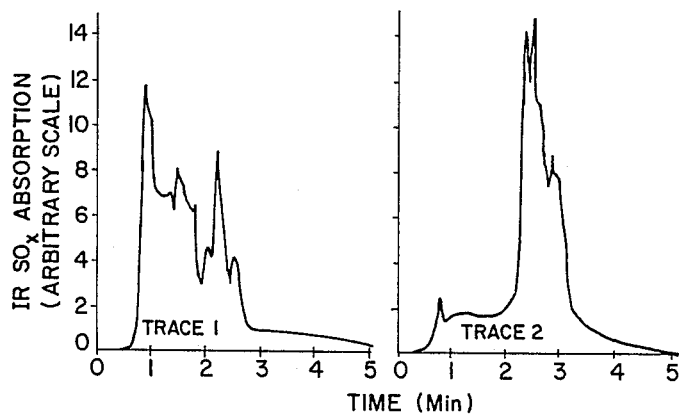
FIG. 2 is two replicate IR spectro-chronograms for $SO_x$ from oxidizing a coal sample without inert diluent.

For the purpose of comparison, a first test was conducted on the above modified analyzer using a sample of coal by itself. The coals used were standard samples from various sources. They were ground to a very fine powder size (−60 μm). Two 100 mg samples of one coal sample were analyzed by being placed in sample boats and analyzed within the modified analyzer at a combustion chamber temperature of 525° C. The results obtained are shown in FIG. 2 and it will be seen that there is very poor reproduction of the spectro-chronograms.

EXAMPLE 2

For this test, one coal sample was obtained and was finely ground to −60 μm particle size. Six 100 mg samples of this coal were prepared and six further samples were prepared consisting of 100 mg of the individual coal powders thoroughly mixed with 900 mg of silica powder (−60 μm). The twelve different samples thus prepared were then tested in the above modified analyzer at a combustion chamber temperature of 525° C. The result obtained are shown in Table 1 below.

TABLE 1

| Coal Sample Number | % Total Sulphur | | Relative Difference |
|---|---|---|---|
| | Coal (100 mg) only | Coal (100 mg) + Silica (900 mg) | |
| 1 | 0.66 ± 0.02 | 0.67 ± 0.01 | +1.5 |
| 2 | 1.01 ± 0.01 | 1.01 ± 0.01 | ±0.0 |
| 3 | 2.12 ± 0.02 | 2.14 ± 0.02 | +0.9 |
| 4 | 2.44 ± 0.05 | 2.43 ± 0.02 | −0.4 |
| 5 | 3.58 ± 0.01 | 3.61 ± 0.05 | +0.8 |
| 6 | 4.54 ± 0.01 | 4.55 ± 0.01 | +0.2 |

From the above results, it will be seen that the total sulphur content was the same, regardless the addition of silica to coal. This clearly shows that silica is inert and does not interfere with the sulphur analysis.

EXAMPLE 3

Figure 3:
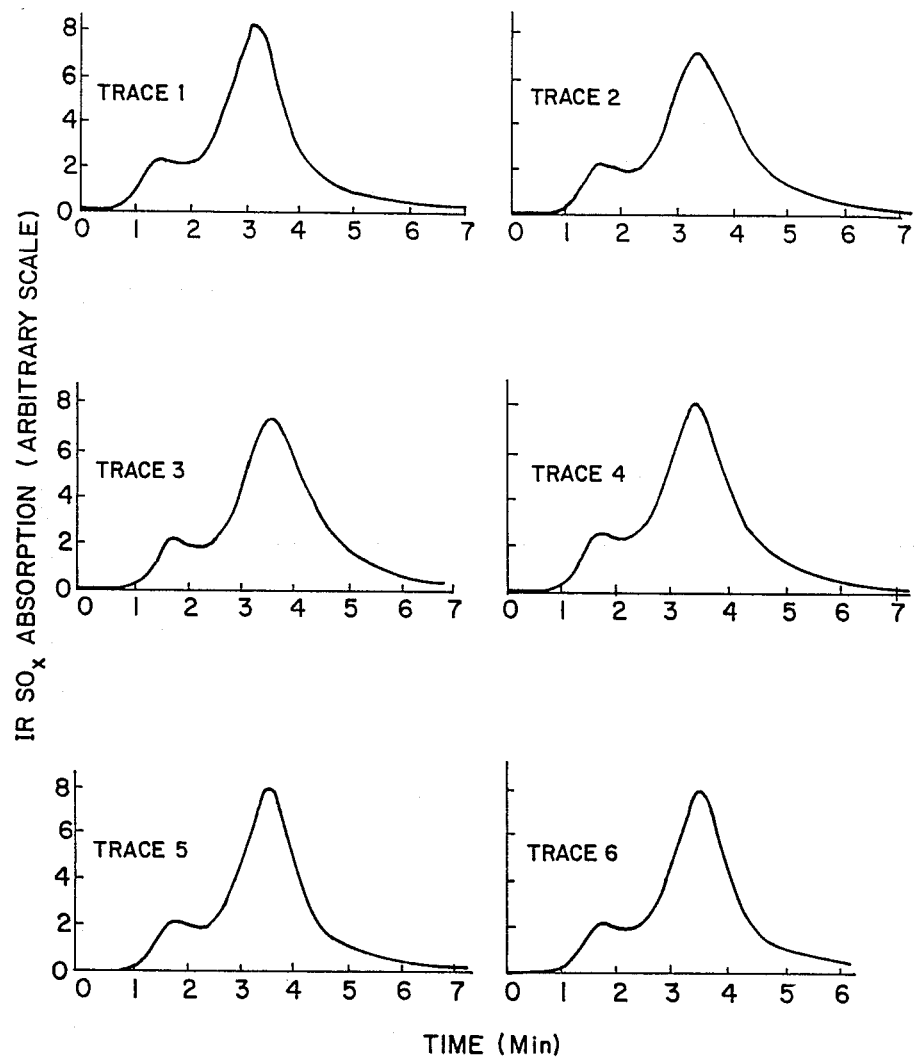
FIG. 3 is six replicate IR spectro-chronograms for $SO_x$ from oxidizing a coal sample with silica diluent.

This test was carried out using a single sample of coal which was ground to a powder of −60 μm particle size. Six samples were prepared each consisting an intimate mixture of 100 mg of the above coal powder and 900 mg of silica powder (−60 μm). The six samples were then each analyzed within the modified analyzer at a combustion chamber temperature of 525° C. The results are shown in FIG. 3 and it will be seen that all six tracings are substantially identical, clearly showing that there is a high level of reproducibility.

EXAMPLE 4

Figure 4:
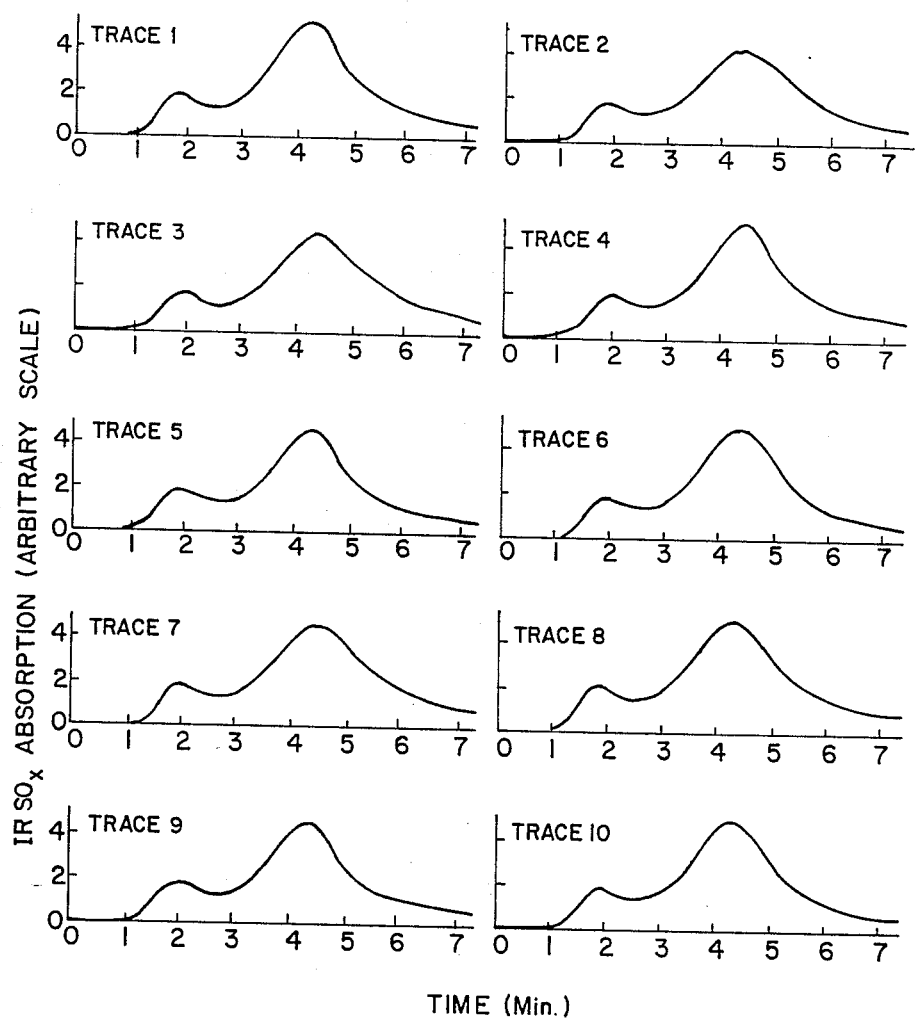
FIG. 4 is ten replicate IR spectro-chronograms for $SO_x$ from oxiding a coal sample with silica diluent.

The same general procedure as described in Example 3 was repeated using samples consisting of 100 mg of the coal powder and 900 mg of the silica powder, but for these tests the combustion chamber temperature was lowered to 500° C. The results for ten replicate tests are shown in FIG. 4 and it will be seen that an excellent reproducibility of sulphur content was obtained as well as excellent definition and separation of the peak positions and heights for the primary and secondary peaks.

EXAMPLE 5

Figure 5:
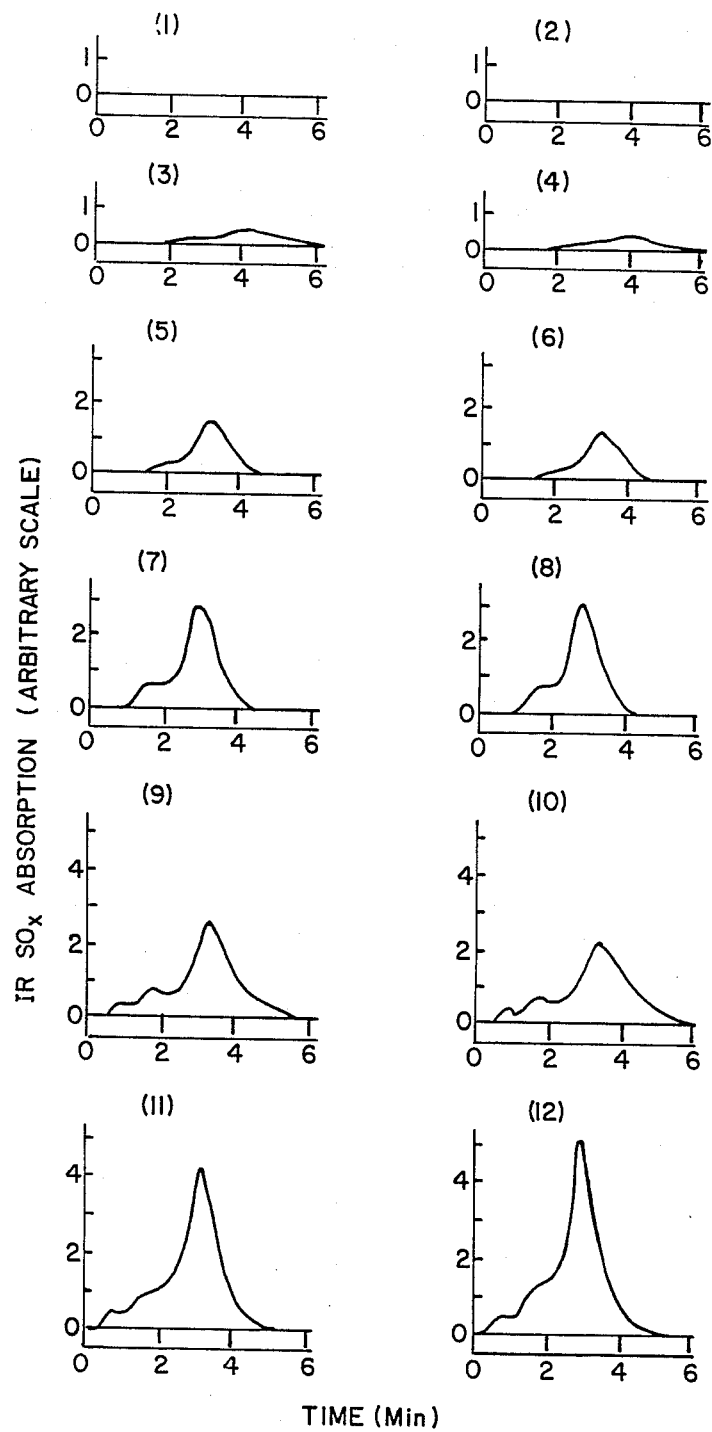
FIG. 5 is duplicate IR spectro-chronograms for $SO_x$ from oxidizing five different coal samples with silica and from silica only.

For this example, five different coal samples were used which were known to vary widely in their amounts of different sulphur forms. The same general procedure as described in Example 3 was used with samples consisting of carefully blended mixtures of 100 mg of coal powder and 900 mg of silica powder. A sample of silica powder only was also tested. The tests were all conducted at a combustion chamber temperature of 550° C. and the results of six duplicate tests are shown in FIG. 5.

Excellent reproducibility was obtained and the spectro-chronogram tracings obtained showed the results in Table 2

TABLE 2

| Trace No. | Sample No. | % Sulphur Forms | | | |
|---|---|---|---|---|---|
| | | Organic | Pyritic | Sulphatic | Total |
| 1 & 2 | Silica only | 0.00 | 0.00 | 0.00 | 0.00 |
| 3 & 4 | Coal S-1 | 0.42 | 0.03 | 0.06 | 0.51 |
| 5 & 6 | Coal S-2 | 0.71 | 0.38 | 0.02 | 1.11 |
| 7 & 8 | Coal S-3 | 0.73 | 1.42 | 0.10 | 2.25 |
| 9 & 10 | Coal S-4 | 1.18 | 1.00 | 0.73 | 2.91 |
| 11 & 12 | Coal S-5 | 1.36 | 2.09 | 0.66 | 4.11 |

The above results clearly show that the reproducible peaks are associated with different forms of sulphur.

EXAMPLE 6

Figure 6:
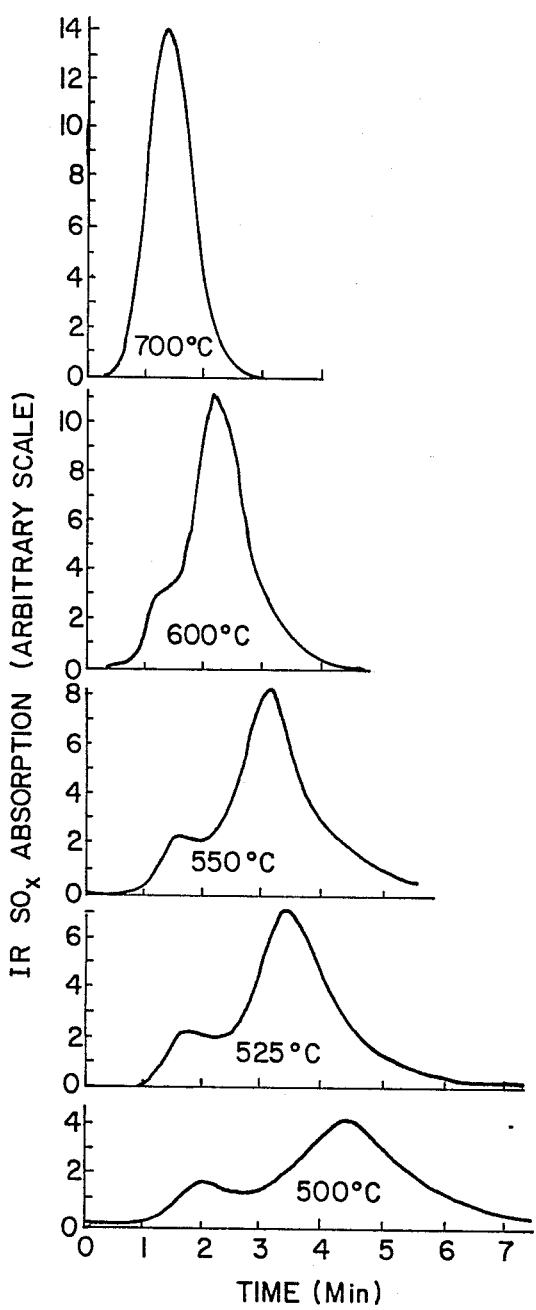
FIG. 6 is IR spectro-chronograms for $SO_x$ from oxidizing coal with silica diluent at different temperatures.

To study the effect of reaction temperature on the shape of the spectro-chronograms, a 100 mg sample of coal (−60 μm) was mixed with 900 mg of silica powder (−60 μm) and analyzed at 500°, 525°, 550°, 600° and 700° C. The results obtained are shown in FIG. 6 and it will be seen that as the reaction temperature increased from 500° to 700° C., the intensity of the primary and secondary peaks grew from about 43.5 to 141.0 mm and from about 17.0 to about 40.0 mm respectively. On the other hand, the peak position shifted from 264 to 84 seconds for the primary peak and from 114 to about 48 seconds for the secondary peak. The changes in peak, height and position were more pronounced for the primary peak than those for the secondary peak. As the reaction temperature increased, the resolution between the primary and secondary peaks became progressively poorer. The same coal sample was used for this complete temperature study and the area under the spectro-chronograms remained unchanged, indicating that the total sulphur content was identical for all cases.

Having thus described the present invention, it should be noted that various other alternatives, adaptations and modifications may be used within the scope of the present invention. For instance, while the description relates primarily to the detection of different forms of sulphur present in coal, the sulphur being detected may be present in many materials other than coal.

We claim:

1. A method for quantitatively determining different forms of sulphur present in a solid matrix, which comprises burning a finely divided sulphur-containing sample having particle sizes of less than 60 μ m within a combustion chamber, said combustion chamber being at a predetermined elevated temperature, continuously removing and collecting combustion gases from the chamber, continuously generating a signal-time pattern indicative of amounts of sulphur dioxide in the collected combustion gas as a function of combustion time of the sulphur-containing sample thereby to obtain peaks in a generated signal-time pattern indicative of different forms of sulphur and determining from the pattern peaks a quantity of each form of sulphur in the sample; characterized in that a finely divided sulphur-containing sample is mixed prior to burning with particles of silica having particle sizes of less than 60 μ m.

2. A method according to claim 1 wherein the sulphur-containing sample is coal.

3. A method according to claim 2 wherein the silica and coal are in the weight ratio of at least 2:1.

4. A method according to claim 3 wherein the weight ratio of silica to coal is in the range of about 5 to 10:1.

5. A method according to claim 2 wherein the combustion chamber is at a temperature in the range of 500° to 2000° C.

6. A method according to claim 1 wherein signal-time pattern is obtained by continuously monitoring intensities of infrared spectra for sulphur oxycompounds.

7. A method according to claim 6 wherein the signals from the infrared intensity monitoring are fed to a microprocessor which receives the infrared intensity-time pattern and determines therefrom the quantity of each form of sulphur in the sample.

8. An apparatus for quantitatively determining different forms of sulphur present in a solid matrix, which comprises: (a) a combustion furnace including a combustion chamber for receiving particles of sulphur-containing material mixed with particles of a solid diluent inert to sulphur under combustion chamber conditions and for combusting said sample to form combustion gases containing sulphur oxycompounds, means for controlling the temperature of the combustion chamber and means for feeding oxygen to the combustion chamber at a controlled rate, (b) conduit means connected to an outlet of said combustion chamber for continuously removing combustion gases from the combustion chamber, (c) detector means for detecting sulphur oxycompounds concentration of gases passing through said conduit and for generating output signals indicative of said concentration at time intervals during substantially the total period of combustion gas production from said sample, and (d) processor means for receiving output signals from (i) said detector means and (ii) time of combustion gas production and determining therefrom the quantity of each form of sulphur in the sample.

9. A method for quantitatively determining different forms of sulphur present in a solid matrix, which comprises burning a sulphur-containing sample having particle sizes of less than 60 $\mu$m within a combustion chamber, said combustion chamber being at a predetermined elevated temperature; continuously removing and collecting gases from the chamber, continuously generating a signal-time pattern indicative of amounts of sulphur dioxide in the collected combustion gas as a function of combustion time of the sulphur-containing sample thereby to obtain peaks in a generated signal-time pattern indicative of different forms of sulphur and determining from the pattern peaks a quantity of each form of sulphur in the sample;

characterized in that said finely divided sulphur-containing sample is mixed prior to burning with particles of a solid diluent inert to sulphur at said combustion chamber elevated temperature, said solid diluent having particle sizes of less than 60 $\mu$m.

* * * * *